United States Patent
Han et al.

(10) Patent No.: US 6,774,646 B1
(45) Date of Patent: Aug. 10, 2004

(54) ELECTRON BEAM INSPECTION SYSTEM USING MULTIPLE ELECTRON BEAMS AND UNIFORM FOCUS AND DEFLECTION MECHANISMS

(75) Inventors: Liqun Han, Santa Clara, CA (US); Mark A. McCord, Mountain View, CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

(21) Appl. No.: 10/058,614

(22) Filed: Jan. 28, 2002

Related U.S. Application Data

(60) Provisional application No. 60/341,348, filed on Dec. 17, 2001.

(51) Int. Cl.[7] ............................................. G01R 31/00
(52) U.S. Cl. ...................................... 324/751; 324/750
(58) Field of Search ................................ 324/750, 751, 324/126–127, 117 R, 117 H; 250/397, 398

(56) References Cited

U.S. PATENT DOCUMENTS 3,715,580 A * 2/1973 Maekawa et al. ........... 250/397
4,209,702 A * 6/1980 Shirai et al. ......... 250/396 ML

OTHER PUBLICATIONS

T. P. Chang et al., "Arrayed miniature electron beam columns for high throughput sub–100 nm lithography", J. Vac. Sci. Technol. B, vol. 10, No. 6, Nov./Dec. 1992, pp. 2743–2747.

E. Yin et al., "Electron optical column for a multicolumn, multibeam direct–write electron beam lithography system", J. Vac. Sci. Technol. B, vol. 18, No. 6, Nov./Dec. 2000, pp. 3126–3131.

T. R. Groves et al., "Distributed, multiple variable shaped electron beam column for high throughput maskless lithography", J. Vac. Sci. Technol. B, vol. 16, No. 6, Nov./Dec. 1998, pp. 3168–3173.

* cited by examiner

*Primary Examiner*—Vinh P. Nguyen
(74) *Attorney, Agent, or Firm*—Beyer, Weaver & Thomas, LLP.

(57) ABSTRACT

A method for inspecting samples uses a multiple beam electron system having a uniform magnetic focusing field. Deflection of the incident electron beams is produced by deflector plates generating an electrostatic deflection force which produces a uniform force on the electron beams. Thermal field emission sources generate incident electron beams towards at least two portions of the sample. A detector array collects multiple detection electrons.

17 Claims, 8 Drawing Sheets

ELECTRON BEAM INSPECTION SYSTEM USING MULTIPLE ELECTRON BEAMS AND UNIFORM FOCUS AND DEFLECTION MECHANISMS

CROSS-REFERENCE TO RELATED APPLICATION

This application takes priority under U.S.C. 119(e) of United States Provisional Application No.: 60/341,348 filed Dec. 17, 2001 entitled, "MULTIPLE ELECTRON BEAM INSPECTION SYSTEM USING UNIFORM FOCUS AND DEFLECTION" by Liqun Han and Mark A. McCord which is incorporated by reference in its entirety for all purposes.

BACKGROUND OF THE INVENTION

The present invention relates generally to producing pattern defect inspection systems for wafers, masks, and reticles. More particularly, the present invention relates to scanning electron microscopes and their use in detecting defects in semiconductors.

Scanning electron microscope systems are conventionally used in semiconductor wafer and reticle inspections. In a conventional application, a beam of electrons is scanned over a sample (e.g., a semiconductor wafer). Multiple raster scans are typically performed over a small area of the sample. The beam of electrons either interact with the sample and cause an emission of secondary electrons or bounce off the sample as backscattered electrons. The secondary electrons and/or backscattered electrons are then detected by a detector that is coupled with a computer system. The computer system generates an image that is stored and/or displayed on the computer system. The signal or image from a pattern on the inspected sample is then compared to a reference signal or image corresponding to the same pattern at another location, another wafer, or stored design data. The defects are identified from the differential signal.

The SEM approach provides superior resolution to optical inspection techniques due to the significantly shorter wavelengths used. However, the conventional SEM single electron beam approach provides a low throughput due to several physical limitations of the system.

The use of the electron beam for inspection permits high resolutions to be obtained due to the small sizes of the beam area focused on the wafer ("spot size"). The high resolutions obtainable come at the expense of the throughput. For example, a 300 mm diameter wafer will require an inordinately long inspection period when a single electron beam inspection technique is used. As feature sizes used in semiconductor devices continue to shrink, the smaller spot size of the single electron beam, for example, as small as 50 mn or less, will aggravate the throughput problems. Presently, sequential scanning using a single electron beam combines mechanical movement of a stage holding the sample in a linear direction and an electrical scan of the beam. Achieving significant improvements using the same sequential scanning methods requires unrealistic speeds for the stage movement or the electrical scan.

Moreover, electron beam currents are limited by space charge effects from negatively charged electrons directed to an area of the inspection sample. A faster inspection scan using an electron beam would require a higher electron beam current. Thus, further reductions in the time required to scan a single pixel are limited by the space charge effect.

Multiple beam inspection systems have been proposed as a solution to many of these problems. However, several technical hurdles have prevented their implementation. An array of multiple columns having individual electron beams requires a large number of controls for each of the beams and wiring for each control. One criterion used in evaluating electron lenses is the spherical aberration of the lens or focusing device. Spherical aberrations are defined as the tendency of the outer zones of the lens to focus more strongly than the inner zone, thus resulting in a diffused focus area rather than a single point of focus. While micro lenses available for use in miniaturized columns in some applications have a small spherical aberration coefficient, it still limits the available current for each column and thus limits the throughput.

What is needed is an apparatus that provides an increased throughput for electron beam scanning while providing a high resolution inspection signal.

SUMMARY OF THE INVENTION

To achieve the foregoing, and in accordance with the purpose of the present invention, a multiple electron beam inspection system using uniform focus and deflection fields is described. The method for inspecting samples uses a multiple beam electron system having a uniform magnetic focusing field. Deflection of the incident electron beams is uniformly produced by deflector plates generating a uniform electrostatic deflection force. Thermal field emission sources generate incident electron beams towards at least two portions of the sample.

In one aspect, a multiple beam electron inspection system generates a first and second incident electron beam from a first and second thermal field emission source. Two polepieces generate a uniform magnetic field to focus the first and second incident electron beams on a sample. A deflector directs the first and second incident electron beams towards the sample and directs a first and second detection electron beam from the sample to a first and second detector.

In another aspect, the deflector is configured to generate a uniform electrostatic deflection field and comprises at least two plates positioned on opposite sides of the incident electron beams.

In another aspect, the first and second incident electron beams are deflected to nominal positions on the detectors using a DC bias voltage applied to the deflector. Electronic scanning is performed by applying an AC voltage to the deflector.

In yet another aspect an electrode is combined with the inspection system to generate a retarding field. The retarding field decelerates the incident electron beams but accelerates the detection electron beams.

These and other features and advantages of the present invention will be presented in more detail in the following specification of the invention and the accompanying figures, which illustrate by way of example the principles of the invention.

BRIEF DESCRIPTION OF THE DRAWINGS

The present invention will be readily understood by the following detailed description in conjunction with the accompanying drawings, wherein like reference numerals designate like structural elements, and in which.

DETAILED DESCRIPTION OF SPECIFIC EMBODIMENTS

Reference will now be made in detail to specific embodiments of the invention. Examples of these embodiments are illustrated in the accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

The present invention provides a multiple electron beam inspection system using a uniform focus and deflection field. Pattern defects existing on a sample are inspected in parallel using multiple finely focused electron beams. The total current is distributed into individual beams, thereby increasing the total current and avoiding the space charge effect limitations present in conventional configurations. Another distinctive feature of the invention is the use of a uniform magnetic field along the electron beam axis for focusing the beams coupled with the uniform electrical field perpendicular to the axis for deflecting the inspection beam. The use of uniform fields across a plurality of electron beams decreases the number of controls significantly while maintaining high performance.

Figure 1A:
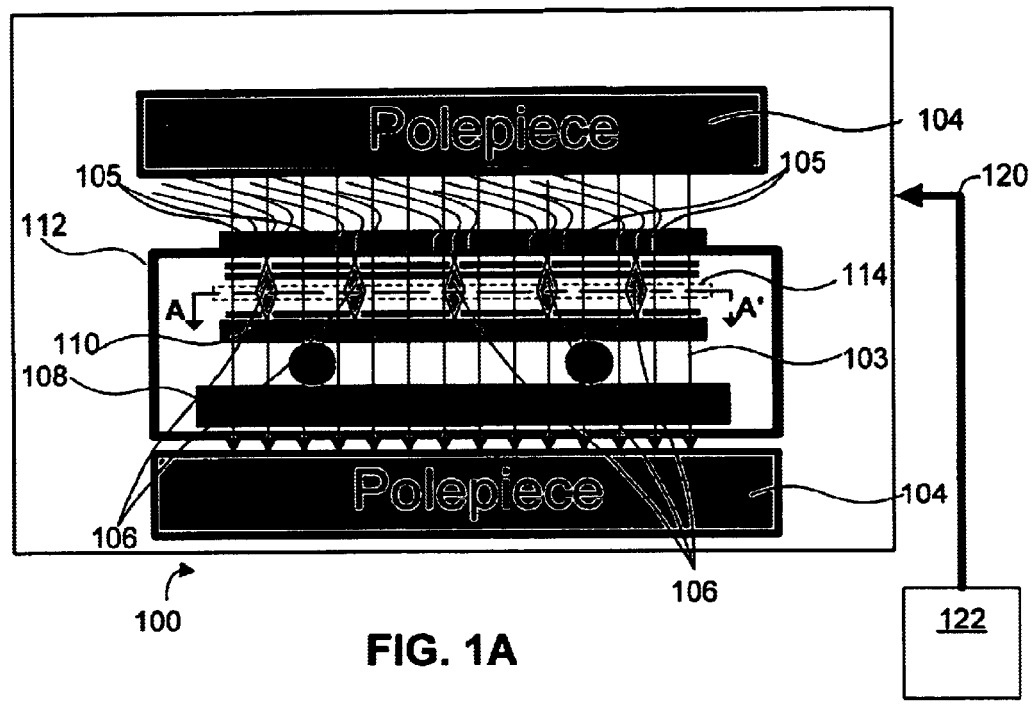
FIG. 1A is a diagrammatic representation of a multiple electron beam inspection system using a uniform focus and deflection field in accordance with one embodiment of the present invention.

FIG. 1A is a diagrammatic representation of a multiple electron beam inspection system 100 using uniform focus and deflection fields in accordance with one embodiment of the present invention. The uniform magnetic field, such as illustrated by representative magnetic field line 103, is generated in the direction of the axis of the electron beam 106. The uniform magnetic field is created by using two polepieces 104, one located above the thermal field emitter sources 105 and one located under the stage 108. The polepiece in one embodiment comprises soft iron or other ferrous material surrounded by copper wire. As is well known to those of skill in the art, application of a current to the wires surrounding the polepiece core produces a magnetic field. Suitable results may be expected from the use of polepieces constructed and configured in a variety of ways and known to those of skill in the art including but not limited to polepieces comprised of ferromagnetic materials to generate the magnetic fields.

The stage 108 is used to move the sample 110 in one direction, for example the y direction of the x-y plane of the sample surface, while an electrostatic deflection field electronically scans the electron beam, generally in an orthogonal direction to the movement of the stage 108 (e.g., the x direction of the x-y plane of the sample). As illustrated, the thermal field emission sources 105 as well as the sample 110 and stage 108 are contained within chamber 112, typically a vacuum chamber to permit precise environmental control of the system during inspection. Electrostatic deflection is performed using deflection plate 114 in combination with a second deflection plate (not shown in FIG. 1A). Pairs of deflection plates may be configured to provide uniform deflection control over a plurality of electron beams. This may be accomplished in one embodiment by positioning a pair of deflection plates each along opposite sides of a row containing a plurality of incident electron beams (from the source to the sample) and detection electron beams (from the sample to the detector). The deflector plates generate an electrostatic field which creates a force which results in uniform deflection in the plurality of incident and detection electron beams.

The thermal field emission source ("Schottky emitter") 105 typically combines a sharp tungsten needle with heating in order to emit electrons. A typical virtual source size is 20 nm with an energy spread of 0.9 eV. The thermal field emission source is conventionally operated in a high vacuum (e.g., $10_{-9}$ Torr.) to minimize current fluctuations. Thermal field emission sources are relatively insensitive to gases in the environment and provide stable operations for extended periods. Their small virtual source size and high brightness also makes them especially suitable for use with embodiments of the present invention. Other source types such as cold field and conventional tungsten emitters may be used in other embodiments of the present invention. Certain operating characteristics of each make them less preferable than thermal field emitters when used with the configurations of the inspection systems of the present invention. For example, cold emitters provide less long term current stability and are more sensitive to contamination by environmental gases.

The column is that part of the system 100 that forms the electron beam and includes normally the electron beam emission sources as well as focussing and deflection mechanisms. The present invention utilizes the polepieces 104 for uniform focusing, thus the polepieces 104 define the vertical limits of the column. The height of the column in the present invention may be varied and still achieve the performance desired by appropriate scaling of the components. For example, approximately equivalent simulation results have been obtained using columns ranging from 5 mm to 2 cm in height with appropriately scaled systems, including scaled column length and beam voltage values. Control signals 120 generated from a computer or CPU or other controller 122 are independently transmitted to the deflection plates 114 and stage 108 to provide control for full inspection coverage over the sample 110.

Figure 1B:
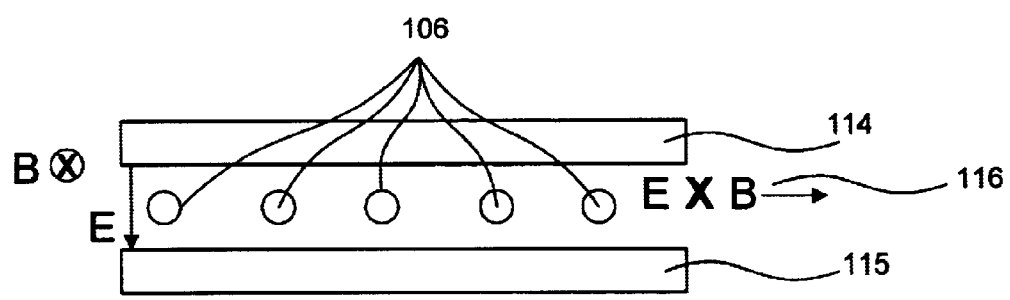
FIG. 1B is a top view of the multiple electron beam inspection system represented in FIG. 1A.

FIG. 1B illustrates a top sectional view of the multiple electron beam inspection system represented in FIG. 1A. This section is taken through the shared deflector plates, as illustrated by line A–A' in FIG. 1A. As illustrated, the electrostatic field is created by the voltage applied to deflector plates 114 and 115. The deflection control is provided by the combined effect of the uniform magnetic field and the uniform electrostatic deflecting field. As well known to those of skill in the relevant arts, these fields produce a net EXB force in an orthogonal direction according to the right hand rule. The resultant EXB force deflects the electron beam 106 in the direction shown by the vector arrow 116 when the electrical (E) and magnetic (B) forces act in the directions shown in the diagram.

Figure 2:
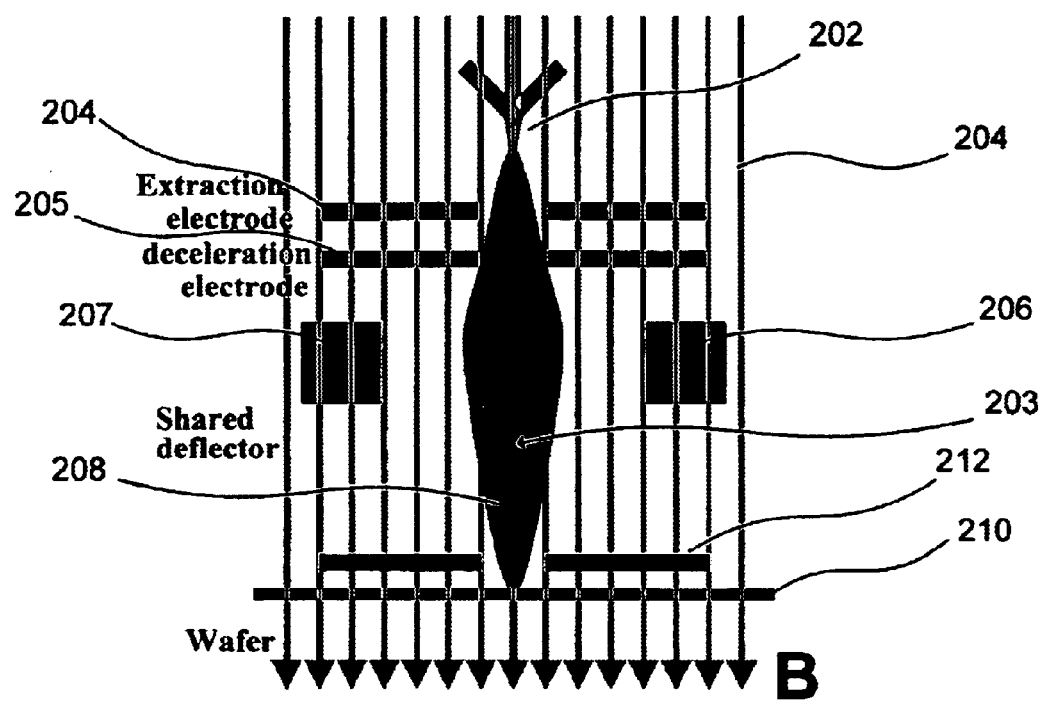
FIG. 2 is an enlarged diagrammatic representation of the multiple electron beam inspection system of FIG. 1 in accordance with one embodiment of the present, invention.

FIG. 2 is an enlarged diagrammatic representation of portions of the multiple electron beam inspection system 100 shown in FIG. 1A. The source for the electron beam is a Shottky tip 202 which is also known as a thermal field emission source. In one embodiment, the tip is automatically positioned with reference to the aperture of the electrodes by mechanical or electrical control. The virtual source of the tip is imaged onto the sample 210 by 1X magnification using the uniform axial magnetic field in combination with an acceleration electrical field generated by the extraction electrode 204. Electron energy in the main beam, i.e., the incident beam directed from the thermal field emission source to the sample, in one embodiment may approximate 4 keV. A second electrode, identified as deceleration electrode 205, is placed between the extraction electrode 204 and the sample 210 to decelerate the electrons in the incident electron beam. The electron energy in this embodiment may, be decelerated to approximately 1 keV.

Electrical scanning of the electron beam is accomplished using an electrostatic deflection field created by the deflector which includes deflection plates 206, 207. In one embodiment, the deflection plates 206, 207 are shared by the neighboring beams. This configuration generates a uniform electrostatic deflection field over the plurality of electron beams sharing the common deflector plates and consequently minimizes the wiring and controls necessary for precise control of multiple electron beams. Though the shared deflectors are shown for illustration purposes on either side of the electron beam 208, in order to generate a lateral movement in the electrical field towards an adjacent electron beam), the deflector plates 206, 207 are placed in front and to the rear of the electron beam, as further illustrated in FIG. 1B.

This system arrangement permits all beams in an array comprising multiple beams to operate under common control, with each individual beam inspecting an individual die on the wafer. The system configuration allows the defects to be identified by comparing the signals from different dice. By electrically scanning the beams and mechanically stepping the stage through the use of a stepper motor, the entire wafer may be inspected with high speed in a parallel manner.

Figure 3:
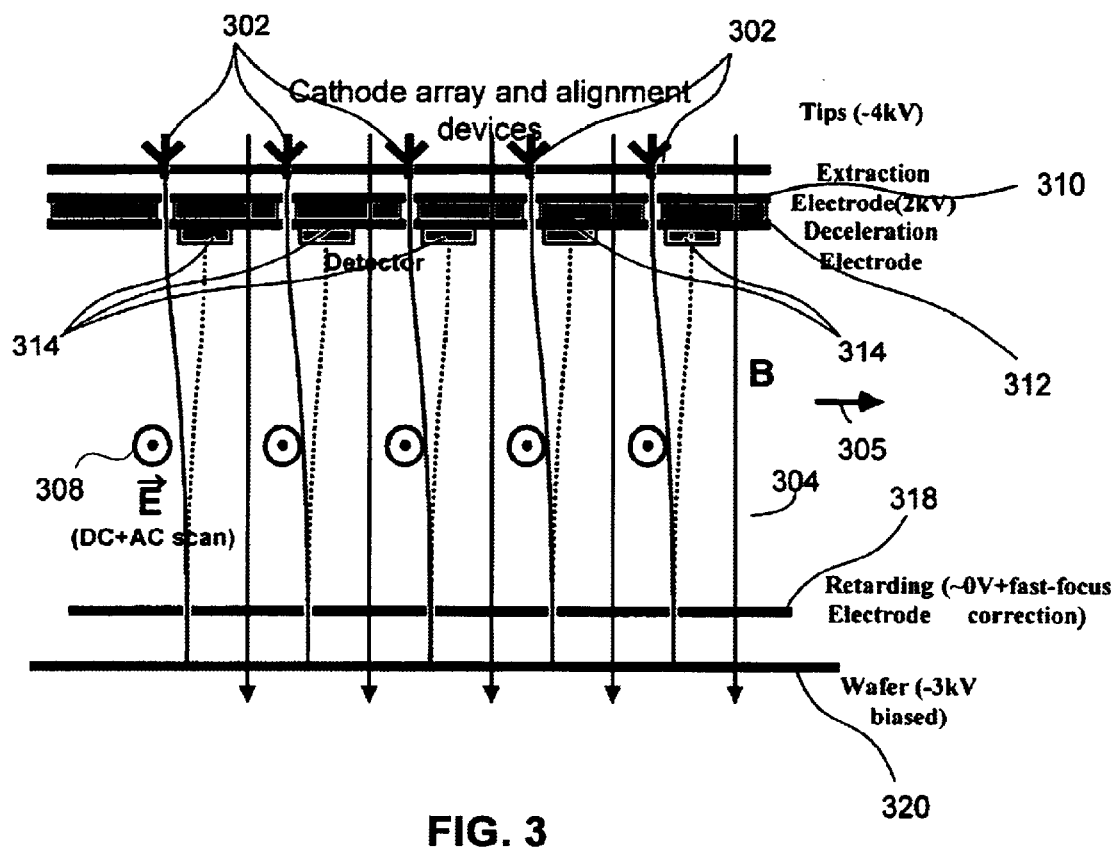
FIG. 3 is a diagrammatic representation of a cathode array and alignment devices in accordance with one embodiment of the present invention.

FIG. 3 is a diagrammatic representation of the cathode array and alignment devices in accordance with one embodiment of the present invention. Multiple Shottky tips 302 are shown within a uniform magnetic field (B) depicted by magnetic field lines 304. The electrostatic deflection field is shown acting in a vector direction out of the drawing as illustrated by electrical field vector 308. The deflection force produced from the combined effect of the electrical and magnetic fields (EXB) is a deflection in the lateral direction 305. In one embodiment, the Shottky tips 302 are charged to −4 kV. Extraction electrode 310 is charged to +2 kV to create a differential extraction voltage of 6 kV. Deceleration electrode 312 is grounded, at the same potential as the detector array 314. A suitable voltage bias value for the wafer 316 is −3 kV.

The retarding electrode 318 decelerates the electron beam prior to the beam striking the wafer 320. Once the electron beam strikes the wafer 320, either secondary or back scattered electrons are emitted and deflected back towards the detector array 314. Initially, these secondary electrons have a very low voltage, on the order of several volts. In many cases, this voltage level will provide an inadequate detector signal. However, the secondary electrons or back scattered electrons output from the wafer and directed towards the detector array 314 are accelerated by the field produced by the retarding electrode 318. The voltage level of the electrons is generally boosted significantly, in the example embodiment illustrated to approximately 3 kV, thus producing a much larger signal more easily detected by the detector array 314. Although the preceding figures illustrate embodiments of an inspection array having a limited number of thermal field emission sources generating a limited number of incident electron beams and detecting the resulting detection electron beams from different portions of the sample, the invention is not so limited. The present invention is intended to apply to all embodiments wherein a multiple beam inspection array or system is used to inspect different portions of a sample in accordance with the techniques described herein. For example, it is expected that a multiple beam inspection array comprising a plurality of thermal field emission sources generating multiple incident electron beams, the inspection array including a plurality of detectors in a detector array to detect detection electron beams output from different portions of the sample, may be suitably sized and configured in accordance with the techniques and structures described herein to have as few as 2 or as many as 100 or even 10,000 or more of each of the sources, beams and detectors and still be in keeping with the spirit and scope of the present invention.

Figure 4A:
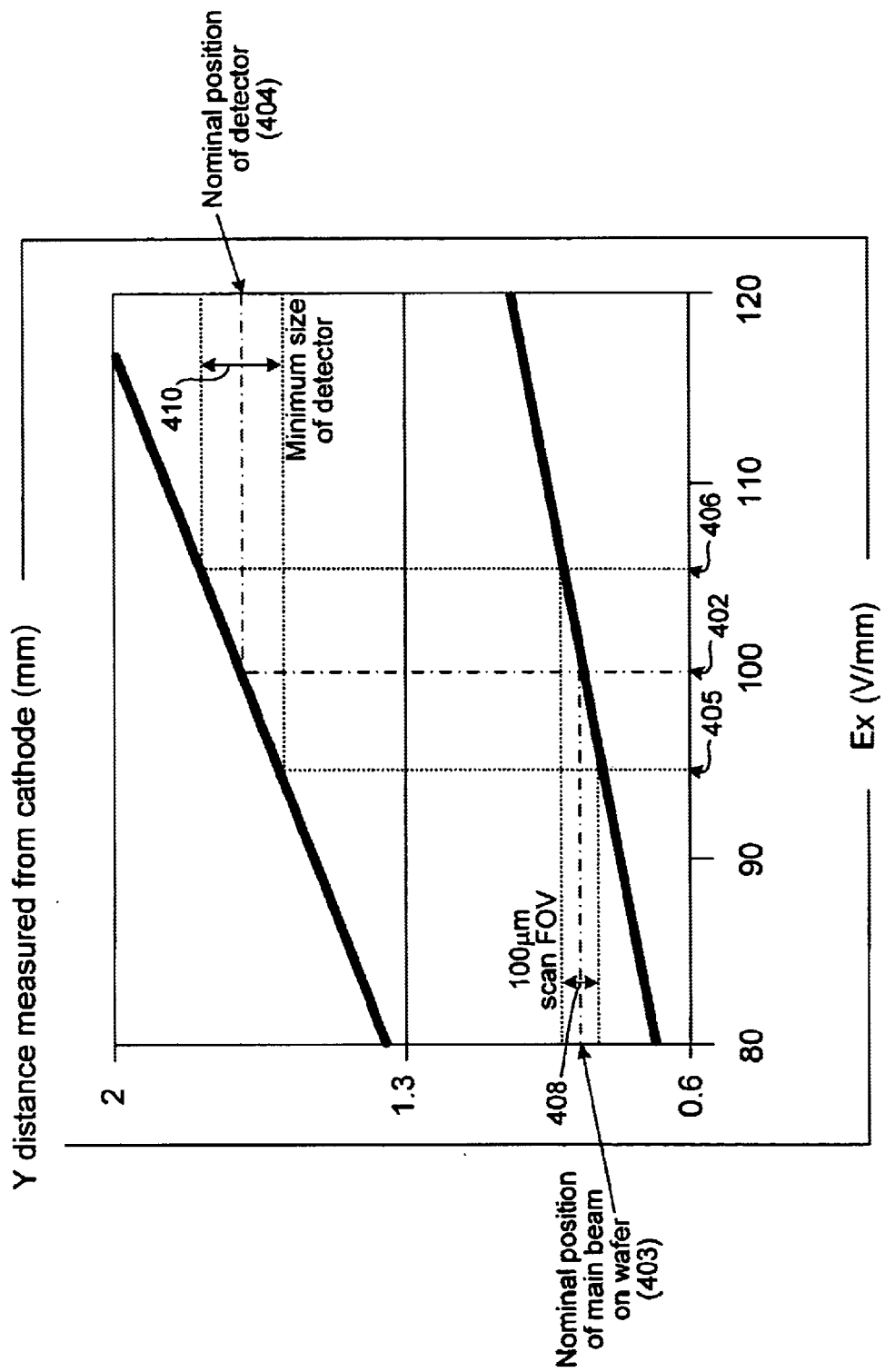
FIG. 4A is a plot depicting the sensitivity of deflection at the detector in accordance with one embodiment of the present invention.

FIG. 4A is a plot depicting the sensitivity of deflection at various points in the multiple electron beam inspection system in accordance with one embodiment of the present invention and reflect simulation results. Sample inspection typically requires that 100 percent of the sample surface be inspected. Full coverage is obtained using a combination of stage movement and electronic scanning. The DC signal provided to the deflector plates provides the deflection to direct the main beam to the sample and the secondary electrons from the sample to the detector. For example, a nominal DC signal component of 100 V/mm, shown at point 402, deflects the main beam to the nominal position on the sample, referenced by point 403 and deflects the secondary electrons to the nominal position at the detector, referenced by point 404. In order to provide full coverage of the sample under inspection, AC signal components (e.g., +or −5 V/nm as shown at points 405, 406) are modulated onto the detector signal to achieve the 100 micron scan Field of View ("TOV") shown at point 408. In order to accommodate the electrostatic deflection induced by these AC components to obtain full inspection coverage, the detector size is required to be much larger than the spot size on the inspected wafer. A suitable spot size for electron beam inspection may be about 50 nm. The scan FOV at 100 microns is considerable larger than the spot size. As shown at point 410, the minimum detector size in the example embodiment is approximately 0.2 mm.

Figure 4B:
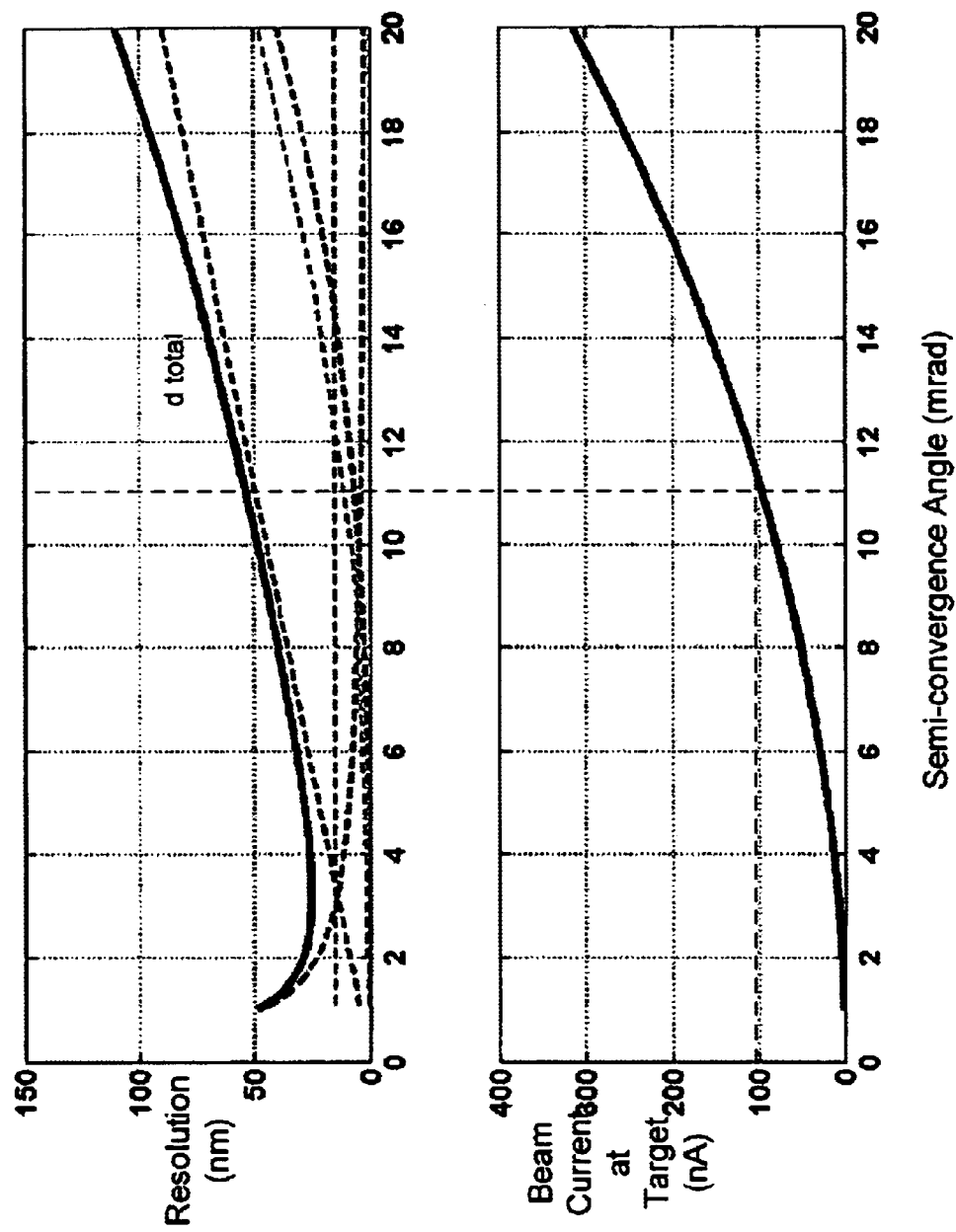
FIG. 4B is a plot depicting the performance evaluation for a single beam of the multiple beam inspection system in accordance with one embodiment of the present invention.

FIG. 4B is a plot depicting the performance evaluation for a single beam of the multiple beam inspection system in accordance with one embodiment of the present invention. A predetermined resolution of 50 nm for the spot size in one embodiment requires a semi-convergence angle of approximately 11 mrad and results in a beam current at the target of approximately 100 nA. The plotted results reflect a cathode having an energy spread of 0.8 eV, a column length of 6 mm, and a beam angular current density of 250 micron A/srad.

Figure 5:
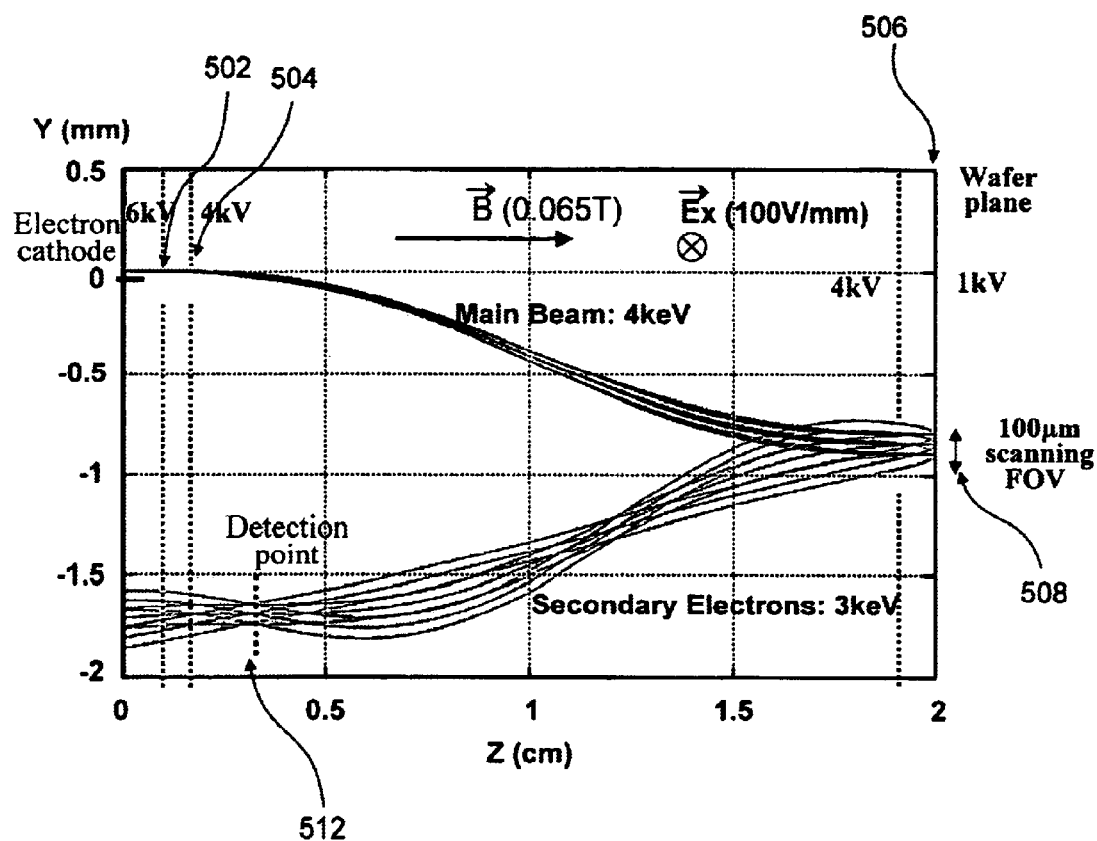
FIG. 5 is a plot depicting the trajectory calculation for secondary electron detection in accordance with one embodiment of the present invention.

FIG. 5 is a plot depicting the trajectory calculation for secondary electron detection in accordance with one embodiment. This plot illustrates that at location 502, the electron beam at the location of the extraction electrode has a potential of 6 kV. At the location of the deceleration electrode, as shown at point 504, the potential is reduced to 4 kV. By the time the impinging electrons strike the sample at the wafer plane, illustrated by point 506, the retarding field has reduced the energy to approximately 1 kV. Space charge interaction between electrons increase the energy spread of the main beam as it moves down the column, which, combined with the energy spread characteristics of the Schottky source (cathode) produce the diffused beam at the wafer plane 506 as illustrated. The resolution achievable is a spot size of 50 nm or less. The electronic deflection of the main beam, from both the DC and AC components results in a field of view ("FOV") of 100 microns. Deflection, as measured along the y axis, from the electron cathode to the sample location is approximately one millimeter. Furthermore, the fine focusing characteristics of the retarding field generated by the retarding electrode enables the impinging electrons to strike the sample with the best focus. The uniform E and B fields lead to a perpendicular landing of the beams on the sample. As further illustrated, the secondary electrons have a potential of 3 kV as a result of the acceleration provided by the retarding field generated by the retarding electrode. Thus, the configuration of the present invention permits a retarding field to reduce the energy of the main beam electrons impinging on the sample and accelerate the secondary and backscattered electrons output from the sample to increase their visibility to the detector array. Detection occurs at detection point 512. As illustrated, the total deflection from the initial position of the electrons at the electron cathode to the detection point approximates two millimeters. The magnitude of the electrostatic field generated will determine the maximum deflection of the electron beams.

Figure 6:
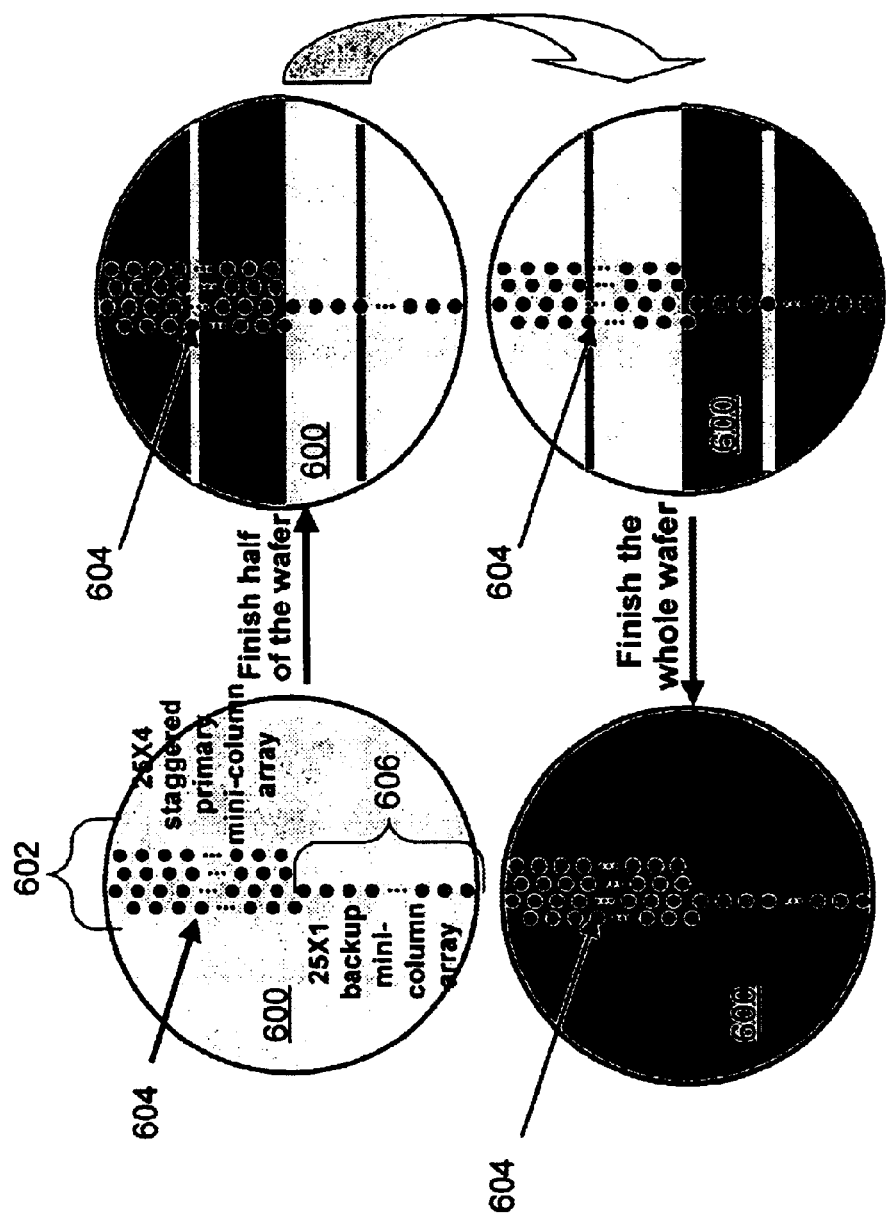
FIG. 6 is a diagrammatic representation of a configuration of a multiple beam inspection array in accordance with one embodiment of the present invention.
Figure 7:
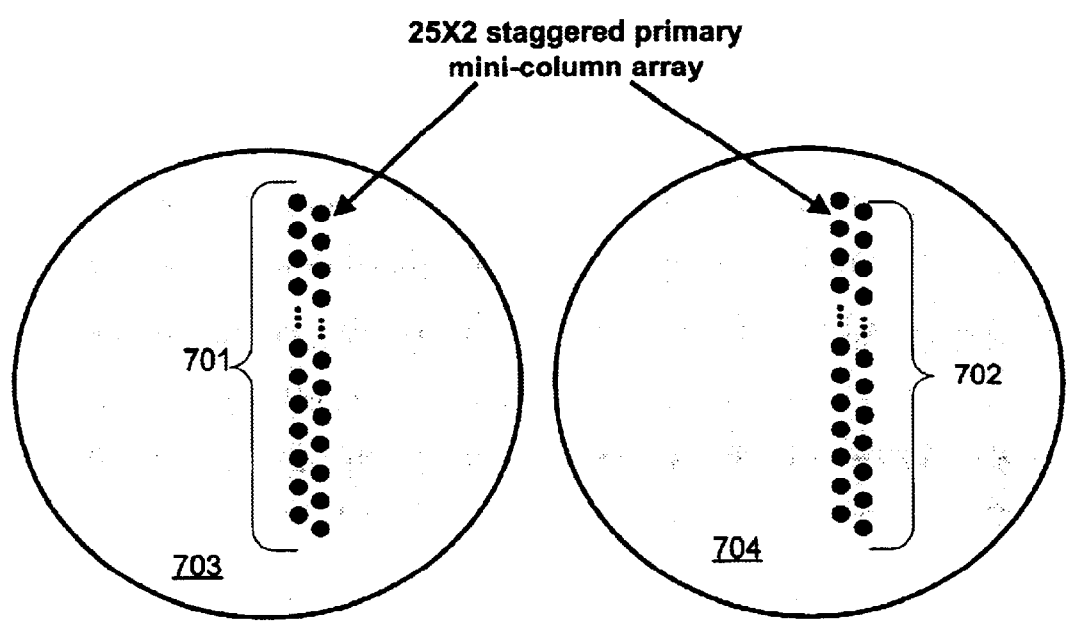
FIG. 7 is a diagrammatic representation of a configuration of a multiple beam inspection array in accordance with another embodiment of the present invention.

FIG. 6 is a diagrammatic representation of a configuration of the multiple beam inspection primary array 602 to provide improved reliability. FIGS. 6 and 7, showing inspection arrays using respectively 100 and 50 of the multiple electron beams as configured and described with reference to FIG. 1A and 1B, are intended to be illustrative and not limiting. Although in one embodiment the beams share one uniform magnetic field created by two polepieces, in other embodiments the array may comprise groups of beams, each of the beams in the group sharing a magnetic field for the group.

The multiple beam inspection array is configured in the example as a 25×4 staggered primary mini column array 602. In one embodiment, the size of the detectors and the size of the electron beam used are such that mechanical movement of the stage in conjunction with electrostatic deflection of the beam in a perpendicular direction to the stage movement permits entire rows of the wafer or other sample to be inspected. In order to provide a raster scan type pattern on the wafer, electrostatic deflection control is provided as a combination of DC bias and an AC signal. The multi-beam inspection array 602 may be used to completely inspect a sample even if one or more beams, such as beam 604, fails. Upon completion of inspection of half of the wafer 600, the wafer may be rotated 180 degrees to permit backup array 606 to inspect the portions of the sample missed as a result of the defective condition of beam 604. In particular, beam 608 in backup array 606 may be used to fill in the holes in coverage resulting from defective beam 604. Backup array 606 must have greater deflection capabilities than primary array 602 due to the array's smaller size. Deflection for backup array 606 may be provided by mechanical or electrostatic deflection or a combination of the two.

FIG. 7 is a diagrammatic representation of a configuration of a multiple beam inspection array in accordance with another embodiment of the present invention.

Two 25×2 staggered primary arrays 701, 702 are used to inspect simultaneously wafers 703, 704. This tandem arrangement of primary arrays 701, 702 improves reliability by continuing inspection with one of the primary arrays should the other fail. Throughput is halved upon failure of one of the primary arrays but is preferable to the use of a single array without backup where the effective throughput (based on full coverage of the wafer) is reduced to zero upon failure of one of the beams.

Although the foregoing invention has been described in some detail for purposes of clarity of understanding, it will be apparent that certain changes and modifications may be practiced within the scope of the appended claims. It should be noted that there are many alternative ways of implementing methods and apparatus of the present invention. For example, the multiple beam arrays using uniform deflection and focussing fields may be configured in alternative patterns or provided with backup arrays different from those illustrated, yet fall within the scope of the present invention. Accordingly, the present embodiments are to be considered as illustrative and not restrictive, and the invention is not to be limited to the details given herein, but may be modified within the scope and equivalents of the appended claims.

What is claimed is:

1. A multiple beam electron inspection system for inspecting a sample, the system comprising:
    a first and a second thermal field emission source to generate a first and a second incident electron beam to be used in inspecting a sample;
    two polepieces positioned to generate a magnetic focusing field that operates to focus the first and the second incident electron beams towards a first and second portion of the sample respectively;
    a first and second detector to detect respectively a first and a second detection electron beam output from the sample that result from the first and the second incident electron beams impinging on the first and second portion of the sample; and
    a deflector shared by the first and second incident electron beams for directing the first and the second incident electron beams towards the first and second portion of the sample and directing the first and second detection electron beams output from the sample towards the detector.

2. The inspection system recited in claim 1 wherein the deflector is configured to generate a uniform electrostatic deflection field.

3. The inspection system recited in claim 1 wherein the deflector comprises at least two deflector plates configured to generate an electric field across the first and second incident electron beams and the first and second detection electron beams.

4. The inspection system recited in claim 2 wherein the deflector is DC biased to guide secondary electrons from the first and second detection electron beams onto the first and second detector.

5. The inspection system recited in claim 2 wherein the deflector is modulated with an AC signal to electronically scan the first and the second incident electron beams across a first and second portion of the sample.

6. The inspection system recited in claim 2 further comprising an electrode to generate a retarding field to accelerate the first and second detection electron beams and to enhance the signals generated from the first and second detector.

7. The inspection system recited in claim 2 wherein a pair of deflector plates are used to provide uniform deflection forces on a row of incident electron beams containing at least a first and a second incident electron beam and a row of detection electron beams containing at least a first and a second detection electron beam.

8. The inspection system recited in claim 2 wherein the first and second detectors are part of an array of detectors arranged in rows.

9. The inspection system recited in claim 5 further comprising a stage to mechanically move the sample with reference to the first and second incident electron beams.

10. The inspection system recited in claim 2 wherein the first and second incident electron beams are part of a plurality of incident beams arranged in rows.

11. The inspection system recited in claim 10 wherein the rows are staggered.

12. A method for measuring a characteristic of a sample using an apparatus that includes a first and second thermal field emission source, two polepieces, a first and second detector, and a deflector comprising:
    causing a first and a second thermal field emission source to generate a first and a second incident electron beam to be used in inspecting a sample;
    focusing the first and the second incident electron beams towards a first and second portion of the sample respectively using two polepieces positioned to generate a uniform magnetic focusing field;
    deflecting the first and the second incident electron beams towards the first and second portion of the sample and deflecting a first and second detection electron beams output from the sample towards first and second detectors using a shared deflector; and
    sensing respectively a first and a second detection electron beam output from the sample that result from the first and the second incident electron beams impinging on the first and second portion of the sample by using the first and second detector.

13. The method recited in claim 12 wherein the deflector comprises at least two deflector plates configured to generate a uniform electric field across the first and second incident electron beams and the first and second detection electron beams.

14. The method recited in claim 12 further comprising using a retarding field to decelerate a first and a second incident electron beam and to accelerate the first and second detection electron beams towards the first and second detectors.

15. A computer program product comprising:
    a computer readable medium having computer program instructions stored within the at least one computer readable product configured to cause a device to be programmed to perform the steps of:
    causing a first and a second thermal field emission source to generate a first and a second incident electron beam to be used in inspecting a sample;
    focusing the first and the second incident electron beams towards a first and second portion of the sample respectively using two polepieces positioned to generate a uniform magnetic focusing field;
    deflecting the first and the second incident electron beams towards the first and second portion of the sample and deflecting a first and second detection electron beams output from the sample towards first and second detectors using a shared deflector; and
    sensing respectively a first and a second detection electron beam output from the sample that result from the first and the second incident electron beams impinging on the first and second portion of the sample by using the first and second detector.

16. The computer program product recited in claim 15 further programmed to use a retarding field to decelerate a first and a second incident electron beam and to accelerate the first and second detection electron beams towards the first and second detectors.

17. The computer program product recited in claim 15 further configured to cause the deflecting through the use of a deflector to generate a uniform electric field across the first and second incident electron beams and the first and second detection electron beams.

* * * * *

UNITED STATES PATENT AND TRADEMARK OFFICE
CERTIFICATE OF CORRECTION

PATENT NO. : 6,774,646 B1
DATED : August 10, 2004
INVENTOR(S) : Han et al.

It is certified that error appears in the above-identified patent and that said Letters Patent is hereby corrected as shown below:

Column 1,
Line 52, change "50mn" to -- 50nm --.

Column 6,
Line 50, change "-5V/nm" to -- 5V/mm --.
Line 53, change "TOV" to -- FOV --.

Signed and Sealed this

Seventh Day of December, 2004

JON W. DUDAS
*Director of the United States Patent and Trademark Office*